United States Patent [19]
Kovalcheck

[11] Patent Number: 5,114,399
[45] Date of Patent: May 19, 1992

[54] SURGICAL DEVICE

[75] Inventor: Steven W. Kovalcheck, San Diego, Calif.

[73] Assignee: Intramed Laboratories, San Diego, Calif.

[21] Appl. No.: 590,930

[22] Filed: Oct. 1, 1990

[51] Int. Cl.⁵ .............................................. A61B 17/20
[52] U.S. Cl. ...................................... 604/22; 606/180; 606/159
[58] Field of Search ..................... 604/22, 19; 606/159, 606/180, 170, 167; 128/753, 752, 751

[56] References Cited

U.S. PATENT DOCUMENTS

| | | | |
|---|---|---|---|
| 4,631,052 | 12/1986 | Kensey | 606/159 X |
| 4,690,140 | 9/1987 | Mecca | 606/159 |
| 4,729,763 | 3/1988 | Henrie | 606/159 X |
| 4,754,755 | 7/1988 | Husted | 604/22 X |
| 4,857,045 | 8/1989 | Rydell | 606/159 X |
| 4,895,560 | 1/1990 | Papantonakos | 606/159 X |

*Primary Examiner*—John J. Wilson
*Assistant Examiner*—Jeffrey A. Smith
*Attorney, Agent, or Firm*—Freilich Hornbaker Rosen

[57] ABSTRACT

A surgical device employs a catheter for removing obstructive material from the body cavity or lumenal passage. The catheter has a blade subassembly on its distal tip for coring, homogenizing, diluting, and aspirating the obstructive material. The obstructive material is homogenized and diluted after it is cored but prior to its aspiration into the catheter. Homogenization and dilution of cored obstructive material is shown to enhance the reliability of the surgical protocol by helping to prevent clogging of the catheter during aspiration.

17 Claims, 4 Drawing Sheets

SURGICAL DEVICE

BACKGROUND

The invention relates to a surgical device for removing obstructive and/or protrusive material from a lumenal passage or cavity within the human body. More particularly, the invention relates to surgical devices which core, homogenize, dilute, and aspirate stenotic or protrusive material. Within the vascular system, the invention relates to atherectomy devices for removing atheromatous and other stenotic material from arteries or to valvectomy devices for removing valves from veins. In other segments of the body, the invention relates to biopsy devices for cutting and removing unwanted materials, projections or outgrowths from various cavities of the body such as the nasal cavity, the synovial cavity and cavum epidural For clarity and simplicity, the invention will be presented as it relates particularly to atherectomy, though applications to other uses will become evident An atherectomy device is a device for surgically removing atheromatous and other stenotic material from blood vessels The performance of an atherectomy can be a useful therapeutic modality for treating occlusive arterial diseases. A number of vascular catheters have previously been developed to facilitate the surgical removal of such obstructive material. For example, one such prior vascular catheter includes a coring device fitted onto its distal end. To remove the obstructive material, the vascular catheter is percutaneously inserted into a blood vessel and guided to the obstructed area by means of medical imaging. Once the obstructed area is reached, the coring device is urged into the obstructive material so as to core through it. If the quantity of obstructive material is relatively small, the obstructive material may be removed by simply withdrawing the catheter. However, if the quantity of obstructive material exceeds the capacity of the coring device, it may be necessary to insert and withdraw the vascular catheter repeatedly. The repeated insertion and withdrawal of a vascular catheter has the potential of damaging the blood vessel and is considered to be medically undesirable.

It has been found that, under some circumstances, cored material may be removed from the vascular catheter by means of aspiration. A coring atherectomy device which includes an aspiration feature for continuously removing cored material is described by Marangoni et al. (U.S. Pat. No. 4,772,258). Marangoni describes a vascular catheter having an aspirating lumen for removing cored material without withdrawing the catheter from the blood vessel. Marangoni discloses that this same lumen can also house a flexible shaft for rotationally driving the coring device so as to facilitate the coring and removing of occlusive material.

Other references disclose that the aspiration process can be improved if the obstructive material is agitated and broken up during the aspiration process. Husted (U.S. Pat. No. 4,754,755) discloses an atherectomy device which agitates and breaks up cored material within the aspiration lumen of the catheter. Husted's coring device is rotationally driven by a wire housed within the aspiration lumen of the catheter. When the wire is rotated, it agitates and breaks up the obstructive material within this aspiration lumen.

It has also been found that the aspiration process can be improved if the occluded area is irrigated while it is being cored. A coring atherectomy device which simultaneously irrigates and aspirates is disclosed by Shiber (U.S. Pat. No. 4,819,634). Shiber's device includes a rotatable hollow tube attached to the coring device and housed within the lumen of the catheter. This rotatable hollow tube serves both as a conduit for aspiration and as a rotational drive for the coring device. Irrigation fluid is conducted to the obstructed site through the lumen of the catheter, i.e. through an annular channel formed by the inner wall of the catheter and outer wall of the rotatable hollow tube. As obstructive material is cored, irrigation fluid is expressed into the blood vessel where it may then be aspirated in conjunction with the aspiration of cored obstructive material into the rotatable hollow tube.

It has also been shown that a hole can be drilled through obstructive material or other stenotic material within a blood vessel and that the drilled material may be irrigated and aspirated away. Moss (U.K. Patent No. 1,235,321) discloses a vascular catheter which contains a transverse blade. The transverse blade is rotationally driven by a hollow tube housed within the lumen of the catheter. Irrigation fluid is conducted to the obstructed site through the hollow tube. As a hole is drilled through the obstructive material, the irrigation fluid and shaving of obstructive material can be aspirated through the lumen of the catheter, i.e. through a space between the outer wall of the hollow tube and the inner wall of the catheter.

SUMMARY OF THE INVENTION

The present invention is directed to a surgical device which employs a catheter to remove obstructive material from body cavities or lumenal passages such as blood vessels by means of coring, homogenization, dilution, and aspiration. More particularly, the surgical device avoids clogging of the catheter by positioning a homogenizing means inside a coring blade and by diluting the homogenized obstructive material therein prior to its entrance into the aspiration channel.

In a preferred embodiment, the homogenizing means includes one or more stages of transverse blades for homogenizing the cored obstructive material so as to transform it into a dilute suspension or emulsion prior to its aspiration. The fluid diluent is preferably released directly into a mixing chamber within the homogenizing means and mixed into the obstructive material as it is homogenized.

Figure 2:
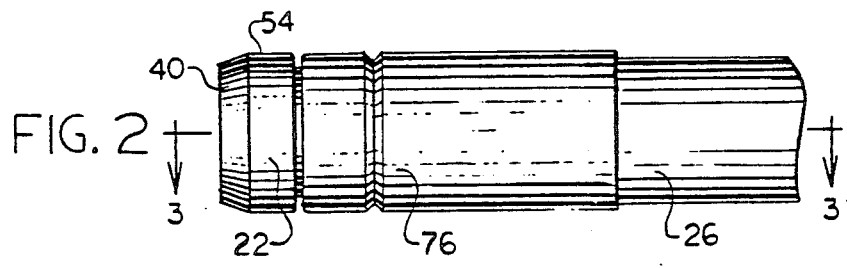
FIG. 2 is a plan view of the preferred surgical device of FIG. 1A illustrating the exterior of the coring blade, the catheter, and a bushing which is attached to the catheter and rotationally coupled to the coring blade.

FIG.'S 7-11 are schematic views illustrating a preferred method, known as atherectomy, employing the device of FIG. 2 for removing obstructive material from a blood vessel. In this representation, a guiding structure is used to direct the surgical device through the obstruction.

Figure 7:
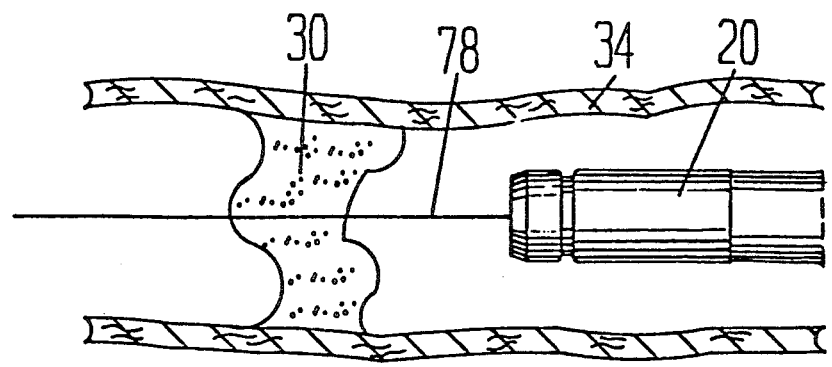

FIG. 7 illustrates the intravascular placement of the surgical device adjacent to the obstructive material prior to the activation of the device.

Figure 8:
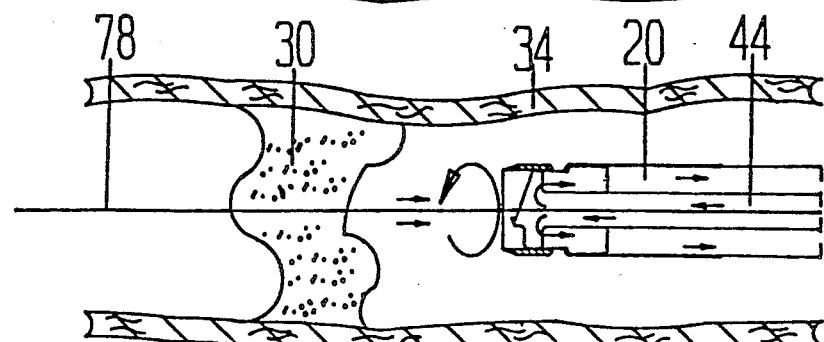

FIG. 8 illustrates the activation of the device, i.e. the expression and aspiration of fluid diluent and the rotational motion of the coring blade and homogenizing means.

Figure 9:
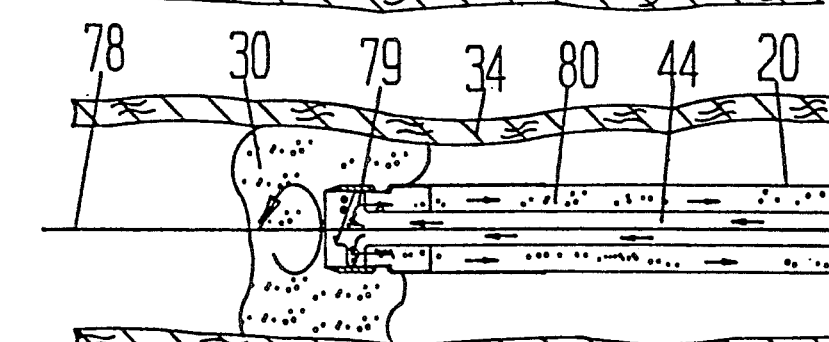

FIG. 9 illustrates the translation of the surgical device into the obstructive material, the coring of the obstructive material, the irrigation and homogenization of the cored obstructive material, and the aspiration of the homogenized obstructive material.

Figure 10:
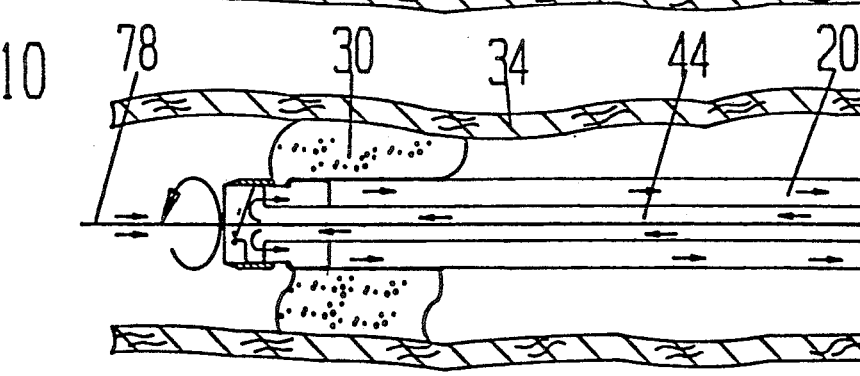

FIG. 10 illustrates the completion of the atherectomizing process.

Figure 11:
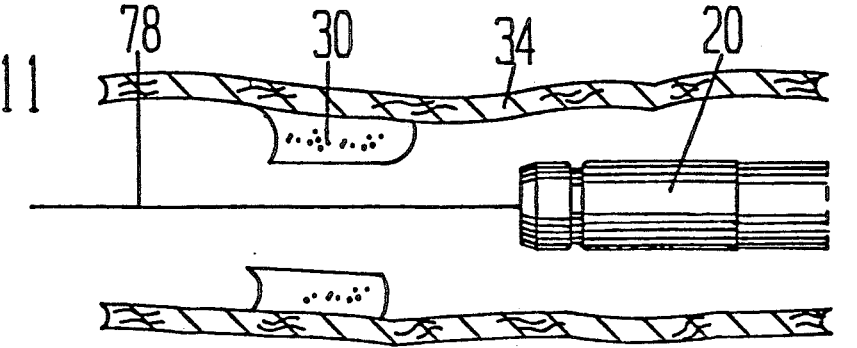

FIG. 11 illustrates the withdrawal of the surgical device from the cored passage formed within the obstructive material.

FIG.'S 12-16 are schematic views illustrating a preferred method employing the device of FIG. 2 for surgically removing obstructive material from other body cavities.

Figure 12:
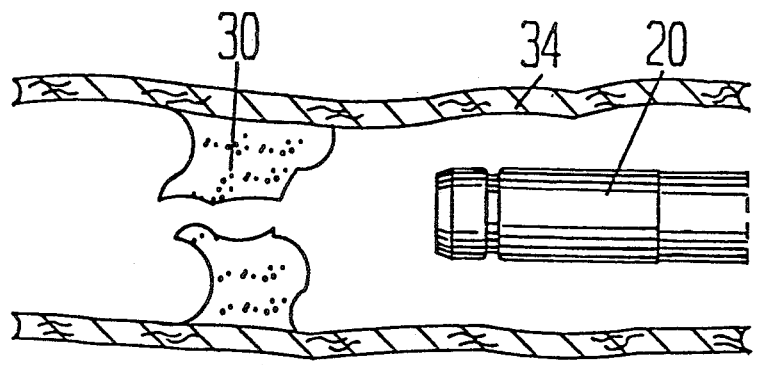

FIG. 12 illustrates the placement of the surgical device within the target cavity and adjacent to the material to be removed prior to the activation of the device.

Figure 13:
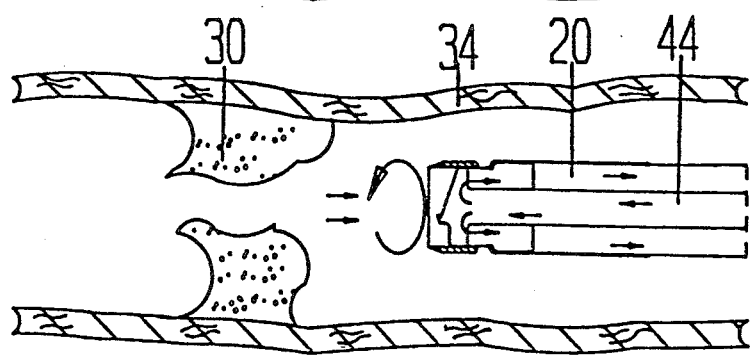

FIG. 13 illustrates the activation of the device, i.e. the expression and aspiration of the fluid diluent and the rotational motion of the coring blade and homogenizing means.

Figure 14:
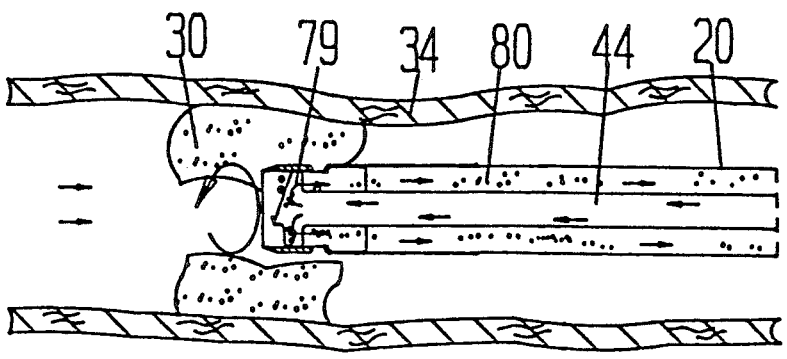

FIG. 14 illustrates the translation of the surgical device into the targeted material, the irrigation and homogenization of the engaged material, and the aspiration of the homogenized engaged material.

Figure 15:
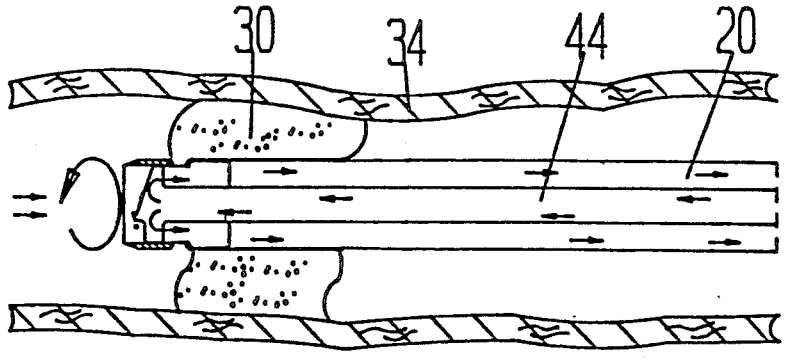

FIG. 15 illustrates the completion of the surgical process.

Figure 16:
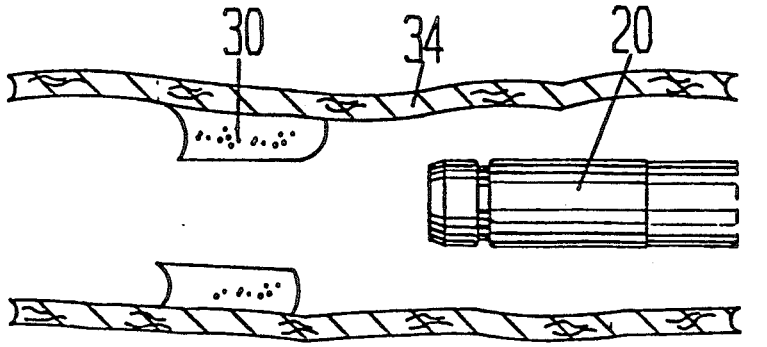

FIG. 16 illustrates the withdrawal of the surgical device from the cored passage formed within the engaged material.

DETAILED DESCRIPTION

The Device

Figure 1A:
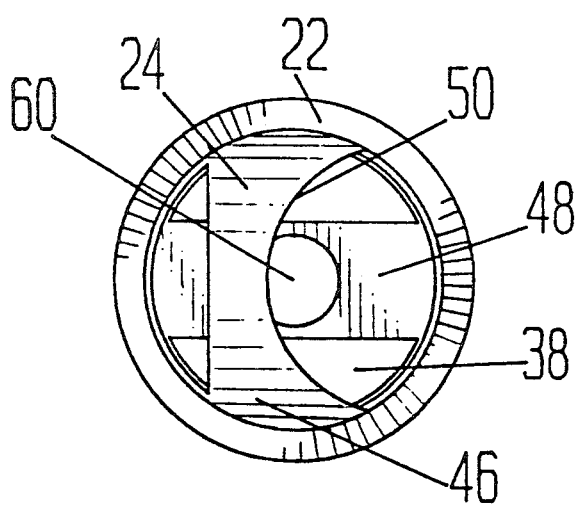
FIG. 1A is a plan view looking into the distal end of a preferred surgical device in accordance with the invention illustrating the interior of the coring blade, the exit of the torque transmitting/irrigation tube, the entrance of the aspiration lumen, and the transverse blades which comprise the homogenizing means.
Figure 1B:
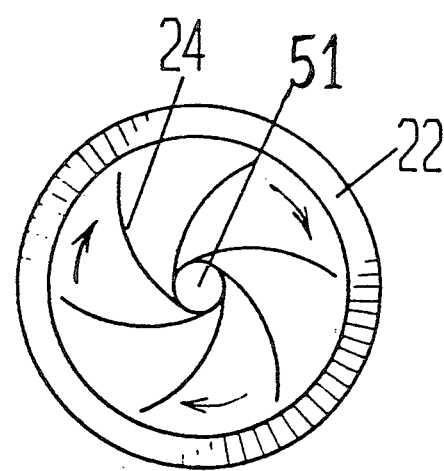
FIG. 1B is a representative plan view looking into the distal end of the preferred surgical device of FIG. 1A depicting the interior of the coring blade and the area swept out by the homogenizing means during blade rotation.
Figure 3:
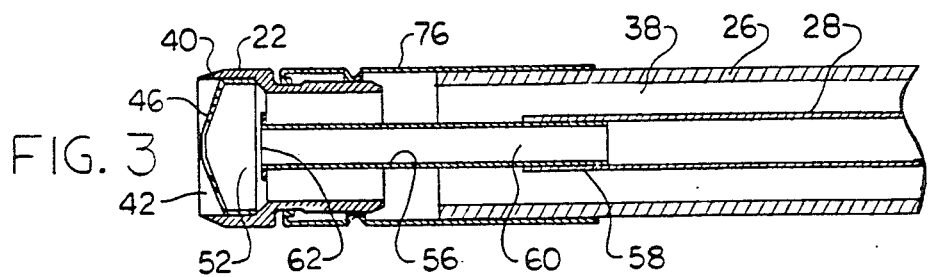
FIG. 3 is a cross section taken along the plane 3—3 of FIG. 2 illustrating the attachment of the homogenizing means to a torque transmitting/irrigation tube housed within the lumen of the catheter.
Figure 4:
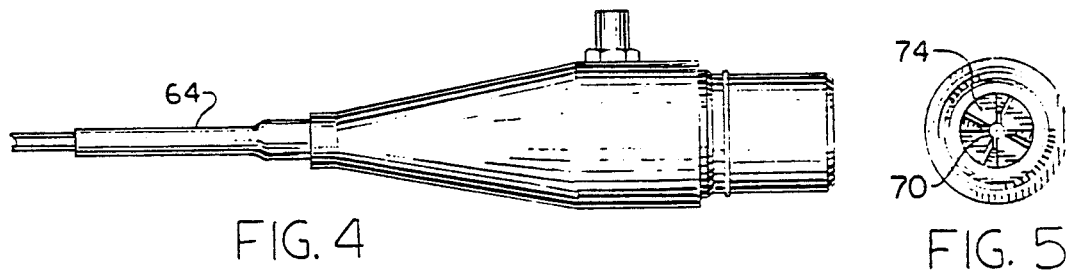
FIG. 4 is reduced plan view of a proximal end of the atherectomy device of FIG. 2 illustrating a coupling unit for coupling the catheter to a rotation drive, an irrigation source, and an aspirator.
Figure 5:
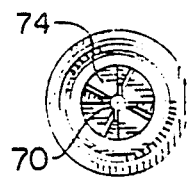
FIG. 5 is a plan view looking into the end of the coupling unit illustrating the fluid entrance to the torque transmitting/irrigation tube and the coupling for the rotational drive.
Figure 6:
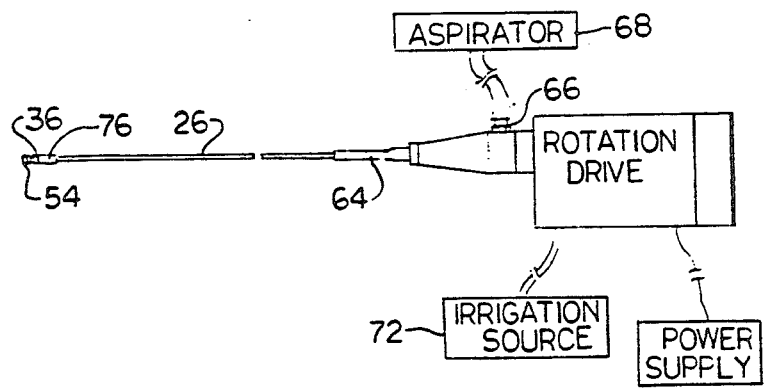
FIG. 6 is a reduced schematic view of the surgical device of FIG.'S 2 and 4 schematically illustrating the aspirator, the irrigation source, and the rotation drive.

A preferred surgical device (20), in accordance with the invention is depicted in FIGS. 1-3 and comprises a (26), and a torque transmitting/irrigation tube (28). The device (20) is useful in various surgical procedures but is particularly suited for atherectomy procedures for removing atheromatous, stenotic, and other obstructive material (30) from blood vessels (34) (FIG. 7). The device (20) removes such obstructive material (30) by means of coring, homogenization, dilution, and aspiration. The coring blade (22) and homogenizing means (24) are coupled to the distal end (36) of the catheter (26). The catheter (26) defines an aspirating lumen (38) for aspirating fluids and for housing the torque transmitting/irrigation tube (28).

The coring blade (22) serves the function of engaging and coring atheromatous, stenotic, and other obstructive material (30) from blood vessels (34). A preferred coring blade (22) has a cylindrical shape and an axially sharpened cutting edge (40) bevelled from outside to inside. The preferred angle of bevel is from 20 degrees to 35 degrees. The bevelled cutting edge (40) provides the coring blade (22) with a good angle of attack for coring obstructive material (30) from the blood vessel (34) but minimizes the probability that the coring blade (22) will inadvertently cut or penetrate the wall of the blood vessel (34). The coring blade (22) is preferably machined from a precipitation hardenable stainless steel material. In use, the coring blade (22) engages obstructive material (30), capturing it in hollow cylindrical passage (42) where it is subject to action by the homogenizing means (24). The coring blade (22) is preferably rotationally driven to facilitate its coring action.

The homogenizing means (24) serves to dice the cored occlusive material (30) into small pieces and to mix the obstructive material (30) with fluid diluent (44) and body fluids so as to form a suspension or emulsion which can be reliably removed by aspiration through the aspirating lumen (38) of the catheter (26). The homogenizing means (24) can take several forms. The homogenizing means (24) is mounted for rotation and nested within the hollow cylindrical passage (42) defined by the coring blade (22). The homogenizing means (24) lies between the cutting edge (40) of the coring blade (22) and the aspirating lumen (38) of the catheter (26) and serves to prevent clogging of both the coring blade (22) and of the aspirating lumen (38). The preferred homogenizing means (24) includes both a primary homogenizing blade (46) and a secondary homogenizing blade (48).

As shown in FIG. 3, the primary homogenizing blade (46), mounted for rotation and nested the hollow cylindrical passage (42) of coring blade (22), performs a first homogenization of obstructive material (30). More particularly, homogenizing blade (46) decomposes engaged material (30) by slicing such material in a plane which is substantially orthogonal to the axis of the coring blade (22). In a preferred embodiment, the primary homogenizing blade (46) has a scythe shaped cutting edge (50) and is attached to the hollow cylindrical passage (42) of the coring blade (22). The scythe shaped cutting edge (50) is oriented in the radial direction from the outside in. The primary homogenizing blade (46) preferably has a generally orthogonal orientation with respect to the axis of the coring blade (22). The preferred cutting edge of the primary homogenizing blade (46) has a 20 degree relief angle and a 20 degree rake angle. It is preferred to mount the primary homogenizing blade (46) in close proximity to the distal end of the coring blade (22), i.e. toward the cutting edge (40) of the coring blade (22). The close proximity of the primary homogenizing blade (46) to the coring blade (22) serves to reduce the possibility that obstructive material (30) engaged within the coring blade (22) will become trapped therein. In a preferred embodiment, the center of the primary homogenizing blade (46) protrudes (rake angle) in an axial direction toward the cutting edge (40) of the coring blade (22) leaving a difference of only 0.020 inch between the axial height of the cutting edge (40) of the coring blade (22) and the upper most cutting edge (50) of the primary homogenizing blade (46). Relief may also be provided on the radial edge of the primary homogenizing blade (46) to prevent the occurrence of stagnation points. The primary homogenizing blade (46) may be machined or otherwise formed from a hard tubular material (30) such as stainless steel.

In a preferred embodiment, the primary homogenizing blade (46) is a scythe shape so as to maximize the length of its cutting edge (50). Note in FIG. 1 that the edge (50) extends radially inwardly toward the central longitudinal axis of the hollow passage (42) but does not cross or impinge upon the central longitudinal axis. Thus, during rotation of the blade (46), a centrally located circular orifice (51) remains unobstructed by the blade.

As illustrated in FIG.'S 1 and 3, the preferred homogenizing means (24) also includes a secondary homogenizing blade (48). The secondary homogenizing blade (48) is mounted for rotation and nested within the coring blade (22) and lies between the primary homogenizing blade (46) and the aspirating lumen (38). The space in the hollow cylindrical passage (42) of the coring blade (22) between the primary and the second homogenizing blades acts as a mixing chamber (52) for mixing decomposed obstructive material (30) with fluid diluent (44) and body fluids. The decomposed obstructive material (30) is irrigated and diluted within this mixing chamber (52) prior to its passage into the aspirating lumen (38). The secondary homogenizing blade (48) is rotationally driven and serves to perform a second homogenization of the obstructive material (30) before such material (30) is suctioned off into the aspirating lumen (38). The secondary homogenizing blade (48) also serves to facilitate the mixing process within the mixing chamber (52).

In the preferred embodiment, the coring blade (22), the primary homogenizing blade (46), and the secondary homogenizing blade (48) are bonded, welded or brazed to one another to form a blade subassembly (54). The blade subassembly (54) is rotationally driven as a unit to perform its coring and homogenizing functions.

As illustrated in FIG. 3, the blade subassembly (54) is rotationally driven by means of its connection to a torque transmitting/irrigation tube (28). The tube (28) is connected to the secondary homogenizing blade (48) by means of an intervening metallic tube (56) of reduced caliper. Alternatively, the tube (28) may be bonded directly to the secondary homogenizating blade (48). The torque transmitting/irrigation tube (28) has an outer wall (58) and an inner cavity (60). The inner cavity (60) communicates with an axial hole (62) in the secondary homogenizing blade (48), either directly or by means of the metallic tube (56), and serves as a conduit for transporting fluid diluent (44). The inner cavity (60) delivers fluid diluent (44) into the mixing chamber (52 between the primary and secondary homogenizing blades (48) within the hollow cylindrical passage (42) of the coring blade (22) for diluting the homogenized obstructive material (30) generated therein. The inner cavity (60) may also be employed for passing a guidewire (78) (FIG. 7), angioscope, or other accessor devices through the catheter (26) into the blood vessel (34). Passage of a guidewire (78) into the blood vessel (34) requires the alignment of the inner cavity (60) of the torque transmitting/irrigation tube (28), the axial hole (62) in the secondary homogenizing blade (48), the hollow cylindrical passage (42) of the coring blade (22) and the orifice (51) swept out by the rotation of the primary homogenizing blade (46). Note that, the scythe shaped cutting edge (50) of blade (46) is displaced from the center of the coring blade (22), as illustrated in FIG. 1, so as to form orifice (51) and allow a guidewire (78) (FIG. 7) to pass the primary homogenizing blade (46). The wall (58) of the torque transmitting/irrigation tube (28) may be extruded or otherwise fabricated from a polymeric material (30) such as polyimide and may include a reinforcing member such as an embedded metallic braid for supporting torque. The wall (58) of the torque transmitting/irrigation tube (28) serves to transmit torque from a rotation drive to the blade subassembly (54). The torque transmitting/irrigation tube (28) maybe housed within the aspirating lumen (38) of the catheter (26) or otherwise incorporated therein.

In the preferred embodiment, the catheter (26) is extruded or otherwise fabricated from an elastomeric plastic material (30) of a durometer approximately 80 Shore A. In another embodiment applicable to other surgical intervention methods, the catheter (26) is formed or otherwise fabricate from materials such as stainless steel which imparts an added stiffness to the catheter. (26) The aspirating lumen (38) of the catheter (26) extends from the proximal end (64) to the distal end (36) of the catheter (26). The distal end (36) of the catheter (26) is designed to pass through a blood vessel (34) or other lumenal channel. The proximal end (64) is designed to remain outside the body. The aspirating lumen (38) and the torque transmitting/irrigation tube (28) housed therein form an annular passage for the aspiration of fluids.

The proximal end (64) of the aspirating lumen (38) is coupled to an aspiration port (66) which can be connected to an aspirator (68). The aspirator (68) suctions fluid from the mixing chamber (52) of the blade subassembly (54), through the aspirating lumen (38). The aspirator (68) may include a reservoir for the collection and/or storage of aspirated fluids. In a preferred embodiment, the aspirator (68) utilizes volume displacement to accurately control the rate of aspiration.

The proximal end of the torque transmitting/irrigation tube (28) is connected to an irrigation port (70) which can be hydraulically connected to an irrigation source (72). In the preferred embodiment, the irrigation source (72) includes a positive displacement pump capable of accurately controlling the rate by which fluid diluent (44) is expressed through the torque transmitting/irrigation tube (28) and into the mixing chamber (52) of the blade subassembly (54).

The proximal end of the torque transmitting/irrigation tube (28) is rotationally coupled to a rotation drive (74). The rotation drive (74) may comprise an electric motor or equivalent rotational driving means.

In the preferred embodiment, the blade subassembly (54) is set into a tubular bushing connector (76) which is bonded to the distal end (36) of the catheter (26). The tubular bushing connector (76) is machined, formed or otherwise fabricated in such a way as to capture the blade subassembly (54) while at the same time allowing free running or rotation of the blade subassembly (54) within the interior of the tubular bushing connector (76). The connection of the blade subassembly (54) and the tubular bushing connector (76) is designed to maintain the concentricity of the blade subassembly (54) while minimizing bearing contact between the two elements. Surface finish of nominal 8 micro inches can also be provided on the mating parts to minimize frictional forces. The tubular bushing connector (76) is bonded, crimped or otherwise attached on its proximal end to the distal end of the outer tube.

The Coring and Homogenization Process

In a significant use of the device (20) as an atherectomy tool, it is inserted percutaneously or intraoperatively into the targeted stenotic or obstructed blood vessel (34) along a guidewire (78) passed through the centrally located torque transmitting/irrigation tube (28). With fluoroscopic assistance the guidewire (78) is positioned through the targeted lesion and the distal end (36) of the catheter (26) is placed in close proximity to the obstructive material (30) by sliding the catheter (26) along the guidewire (78). The proximal end (64) of the catheter (26) is connected to the support systems, i.e. the torque transmitting/irrigation tube (28) is hydraulically connected to the irrigation source (72); the annular channel within the aspirating lumen (38) of the catheter (26) is connected to the aspirator (68); and the torque transmitting/irrigation tube (28) is rotationally connected to the rotation drive (74). Preferably the rotation drive (74) should be capable of driving the torque transmitting/irrigation tube (28) at 5000 RPM.

After the catheter (26) has been properly positioned within the blood vessel (34) under fluoroscopic guidance, the physician may activate a switch which simultaneously activates the irrigation and aspiration units (68 & 72) and the rotation drive (74). The torque generated by the rotation drive (74) unit is transmitted via the torque transmitting/irrigation tube (28) to the blade subassembly (54). After the device is activated, the physician proceeds to advance the device axially along the guidewire (78) through the obstructive material (30). As a result of this axial translation the obstructive material (30) is engaged and cored by the cutting edge (40) of the coring blade (22). Cored material (30) is then sliced in a generally orthogonal plane by the cutting edge (50) of the primary homogenizing blade (46) so as to form a suspension or emulsion of sliced material (79). Cored material which may wrap about the centrally located guidewire (78) may be engaged and removed by the wiping action of the radially inwardly directed edge (50) of the primary homogenized blade (46) as the catheter (26) is advanced over the guidewire (78).

The suspension or emulsion of sliced material (79) then passes into the mixing chamber (52) of the blade subassembly (54). Fluid diluent (44) is introduced into the mixing chamber (52) in order to dilute the sliced material (79). The sliced material (30) is further mixed and homogenized by a secondary homogenizing blade (48) before it is then drawn by negative pressure into the annular channel of the aspirating lumen (38). If the target obstructive material (30) does not fully occlude the blood vessel (34) or a body cavity, blood or other body fluids may enter the catheter (26) to further contribute to the dilution of the particles during homogenization.

The rotation of the blade subassembly (54) also serves to create a centrifugal force which is transferred to the particulates within the suspension or emulsion of sliced material (79). This centrifugal force tends to push the particulates in a radially outward direction toward the outer wall of the annular channel.

Once the mixture of homogenized occlusive material (79) and diluent (44) enters the aspiration lumen (38), it is suctioned out and collected in a reservoir exterior to the patient. The optimal rate at which the device can engage obstructive material (30), i.e. the optimal rate at which the device can be advanced within the obstructive material (30), is dependent upon a balance between the flow rate of the fluid diluent (44), the flow rate of aspiration, the rate of homogenization, and the relative dimensions of both the aspiration lumen (38) and the torque transmitting/irrigation tube (28).

In another significant use of the device (20) as a biopsy tool, it is inserted in the same manner as described above but without the centrally located guidewire (78). The distal end (36) of the catheter (26) may be located adjacent to the obstructive target material using an endoscope passed through the centrally located torque transmitting/irrigation tube (28). The endoscope is then removed prior to activation of the surgical device. The engagement, coring and homogenizing of the target material then proceeds as described above.

Hydrodymanics of the Aspiration Process

The surgical device (20) described above effectively and safely engages, cores, and homogenizes obstructive or protrusive material (30). The homogenized material (80) is then diluted and aspirated out the target artery. Successful removal of the obstructive material (30) requires both proper homogenization and proper aspiration. Proper aspiration of the material (79) is dependent upon the fluid mechanics of the system, the dimensions of the tubular elements of device (20), and the rate at which target material (30) is engaged by the coring blade (22). Particles must be carried in a dilute suspension within the annular channel of the aspirating lumen (38) in order to achieve successful removal. Empirical work supports the need for a particle concentration of 20% or less by volume and particle size significantly less than the cross sectional gap of the aspiration annulus. Since stenotic blockage can be complete or nearly complete, i.e. there is little or no body fluid to contribute to particle dilution, it is often necessary to provide all of the fluid diluent (44) required to insure a proper dilution of the suspension of particles. On the other hand, it is important not to over irrigate the homogenized particles. Over irrigation can lead to the loss of cut particles back into the blood stream or cavity. Accordingly, the exit velocity of fluid diluent (44) should be less than or equal to the entrance velocity of the aspirated suspension.

Preferably the inner diameter of the coring blade (22) and its advance rate are matched to an irrigation system providing a diluent volume flow rate of five or more times the material (30) volume engagement rate. The speed of rotation of the blade subassembly (54) is chosen such that the cored material (30) entering the hollow cylindrical passage (42) of the coring blade (22) has a small particle size to enhance removal. The radial dimensions of the irrigation channel and the aspiration annular channel and the aspiration and irrigation rates are chosen such that the mean exit velocity of the fluid diluent (44) is matched to the entrance velocity of the aspirated suspension of cut material (30). To a first approximation, the system is designed such that the following conditions hold, viz.:

1. $Q_m = 2\pi (R_o - r_1)^2 * L/t$
2. $Q_m < 0.2 * Q_i$

3A. $Q_a \geq B * Q_i$ where $B = \dfrac{R_1^2 * (a_a^2 - 1)}{r_1^2 * (a_i^2 - 1)}$ 3B. $Q_a \geq A * Q_i$ where $A = \dfrac{R_1^2}{r_2^2}(a_a^2 - 1)$ with L is the length of the stenotic lesion
T is the time taken to traverse the lesion
$R_0$ is the inner radius of the primary coring blade
$r_1$ is the outer radius of the guidewire
$r_2$ is the inner radius of the torsional inner catheter
$R_1$ is the outer radius of the torsional inner catheter
$R_2$ is the inner radius of the outer catheter
$a_i = r_2/r_1$
$a_a = R_2/R_1$
$Q_m$ is volume flux of engaged atheromatous material
$Q_i$ is the irrigation volume flow rate
$Q_a$ is the aspiration volume flow rate In the preferred embodiment, the surgical device satisfies equations 1, 2, and 3A when a guidewire (78) is used and equations 1, 2, and 3B with $r_1 = 0$ when no guidewire is used. The aspiration rate is chosen high enough that the particle laden fluid (80) behaves Newtonian and no particle settling occurs. The irrigation rate is then chosen such that the exit velocity of the irrigation fluid matches the entrance velocity of the aspiration fluid. Tubing dimensions are then chosen to satisfy equations 1 and 3. The rotational speed of the blade subassembly (54) may be set at 5000 RPM. Following activation, the physician advances the surgical device axially through the obstructive material (30) at a maximum rate of 20 centimeters per minute. This advance rate is sufficiently low such that the removal of the homogenized particles is uncompromised. The size of preferred devices (20) used for atherectomy can range from 5 French to 13 French or its equivalent, viz. 1.6 millimeters to 4.3 millimeters.

What is claimed is:

1. A surgical device for coring, homogenizing, and aspirating obstructive material from a body cavity or lumenal passage with the aid of a fluid diluent, the device comprising:
   a catheter having a proximal end and distal end and defining an aspirating lumen extending therebetween, the distal end for passing into the cavity, the proximal end for remaining outside the cavity,
   a coring blade defining a hollow cylindrical passage for coring the obstructive material from the cavity, said coring blade being coupled to and extending from the distal end of said catheter,
   an irrigation tube incorporated within said catheter for conducting fluid diluent from the proximal end into the hollow cylindrical passage of said coring blade,
   homogenizing means mounted for rotation and nested within the hollow cylindrical passage of said coring blade for homogenizing the cored obstructive material therein in conjunction with the fluid diluent conducted thereto, and means for rotationally driving said homogenizing means within said coring blade.

2. A surgical device as described in claim 1 wherein:
   said homogenizing means including a primary homogenizing blade rotatable within the hollow cylindrical passage of said coring blade and having a substantially orthogonal cutting angle with respect to said coring blade for performing a primary homogenization of the occlusive material therein.

3. A surgical device as described in claim 2 wherein:
   said homogenizing means including a second homogenizing blade positioned between said primary homogenizing blade and the distal end of said catheter for homogenizing the obstructive material and mixing the obstructive material with the fluid diluent prior to aspiration into the aspirating lumen of said catheter.

4. A surgical device as described in claim 1 further comprising:
   an aspiration port connected to the aspirating lumen of said catheter for suctioning homogenized obstructive material therefrom.

5. A surgical device for coring, homogenizing, and aspirating obstructive material from a body cavity or lumenal passage with the aid of a fluid diluent, the device comprising:
   a catheter having a proximal end and a distal end and defining an aspirating lumen extending therebetween, the distal end for passing into the body cavity, the proximal end for remaining outside the body cavity,
   coring blade defining a hollow cylindrical passage and a cylindrical axis for coring the obstructive material from the body cavity, said coring blade being coupled to and extending from the distal end of said catheter,
   a torque transmitting/irrigation tube housed within the aspirating lumen of said catheter for conducting fluid diluent from the proximal end to the distal end of said catheter into the hollow cylindrical passage of said coring blade, and
   homogenizing means mounted for rotation and nested within the hollow cylindrical passage of said coring blade and connected to said torque transmitting/irrigation tube for homogenizing the cored obstructive material within the hollow cylindrical passage of said coring blade in conjunction with the fluid diluent conducted thereto in preparation for suctioning therefrom through the aspirating lumen of said catheter.

6. A surgical device as described in claim 5 wherein:
   said coring blade having a cylindrically shaped cutting edge positioned distally with respect to the distal end of said catheter for coring the occlusive material,
   said homogenizing means including a primary homogenizing blade having a scythe shaped cutting edge nested within the hollow cylindrical passage of said coring blade and having a generally orthogonal orientation with respect to the cylindrical axis of said coring blade for performing a preliminary homogenization of cored obstructive material within the hollow cylindrical passage of said coring blade, said primary homogenizing blade protruding in the direction of the cutting edge of said coring blade.

7. A surgical device as described in claim 6 wherein:
   said torque transmitting/irrigation tube and said coring blade being axially aligned and having a configuration for passing a guidewire or other elongated instrument therethrough, the scythe shaped cutting edge of said primary homogenizing blade having a configuration for allowing the guidewire or other elongated instrument to pass through both said torque transmitting/irrigation tube and said coring blade.

8. A surgical device as described in claim 7 wherein:

said homogenizing means including a second homogenizing blade positioned between said primary homogenizing blade and the distal end of said catheter for homogenizing the obstructive material and mixing the obstructive material with the fluid diluent prior to aspiration into the aspirating lumen of said catheter.

9. A surgical device as described in claim 7 further comprising:

an aspiration port connected to the aspirating lumen of said catheter for suctioning homogenized obstructive material therefrom.

10. A surgical device for coring, homogenizing, and aspirating obstructive material from a body cavity or lumenal passage with the aid of a fluid diluent, the device comprising:

a catheter having a proximal end and a distal end and defining an aspirating lumen extending therebetween, the distal end for passing through the body cavity, the proximal end for remaining outside the body cavity, a tubular bushing connector attached to the distal end of said catheter and extending therefrom, a coring blade defining a hollow cylindrical passage, a cylindrical axis, and a cutting edge for coring the obstructive material from the body cavity, said coring blade being set within the tubular bushing connector, extending distally therefrom, and freely rotatable therein, homogenizing means mounted for rotation and nested within the hollow cylindrical passage of said coring blade and bonded thereto for homogenizing the obstructive material therein, and a torque transmitting/irrigation tube housed within the aspirating lumen of said catheter for conducting fluid diluent from the proximal end to the distal end for irrigating said homogenizing means, said torque transmitting/irrigation tube being rotationally coupled to both said coring blade and said homogenizing means for rotationally driving same, said coring blade, when translationally and rotationally driven, for serving to core the obstructive material, said homogenizing means, when rotationally driven, for homogenizing and mixing obstructive material within the hollow cylindrical passage of said coring blade with the fluid diluent in preparation for aspiration.

11. A surgical device as described in claim 10 wherein:

said homogenizing means including a primary homogenizing blade having a scythe shaped cutting edge nested within and attached to the hollow cylindrical passage of said coring blade and having a generally orthogonal orientation with respect to the cylindrical axis of said coring blade for performing a preliminary homogenization of cored obstructive material within the hollow cylindrical passage of said coring blade.

12. A surgical device as described in claim 11 wherein:

said torque transmitting/irrigation tube and said coring blade being aligned and having a configuration for passing a guidewire therethrough, the scythe shaped cutting edge of said primary homogenizing blade having a configuration for allowing the guidewire to pass through said coring blade.

13. A surgical device as described in claim 12 wherein:

said primary homogenizing blade protruding in the direction of the cutting edge of said coring blade.

14. A surgical device as described in claim 11 wherein:

said homogenizing means including a second homogenizing blade positioned between said primary homogenizing blade and the distal end of said catheter for homogenizing the obstructive material and mixing the obstructive material with the fluid diluent prior to aspiration into the aspirating lumen of said catheter.

15. A surgical device for coring, homogenizing, and aspirating obstructive material from a body cavity or lumenal passage with the aid of a fluid diluent, the device comprising:

a catheter having a proximal end and a distal end and defining an aspirating lumen extending therebetween, the distal end for passing through the body cavity, the proximal end for remaining outside the body cavity, a tubular bushing connector attached to the distal end of said catheter and extending therefrom, a coring blade defining a hollow cylindrical passage and a cylindrical axis with a cutting edge for coring the obstructive material from the body cavity, said coring blade being set within the tubular bushing connector, extending distally therefrom, and freely rotatable therein, homogenizing means including a primary homogenizing blade and a secondary homogenizing blade, said primary homogenizing blade having a scythe shaped cutting edge nested within and attached to the hollow cylindrical passage of said coring blade and having a generally orthogonal orientation with respect to the cylindrical axis of said coring blade for performing a preliminary homogenization of cored obstructive material within the hollow cylindrical passage of said coring blade, said primary homogenizing blade protruding in the direction of the cutting edge of said coring blade, said secondary homogenizing blade nested within and attached to said coring blade and having a generally orthogonal orientation with respect to the cylindrical axis of said coring blade for performing a secondary homogenization of the obstructive material within the hollow cylindrical passage of said coring blade, and a torque transmitting/irrigation tube housed within the aspirating lumen of said catheter for conducting fluid diluent from the proximal end to the distal end of said catheter for irrigating the homogenized obstructive material generated within the hollow cylindrical passage of said coring blade, said torque transmitting/irrigation tube being rotationally coupled to both said coring blade and said homogenizing means for rotationally driving same, said torque transmitting/irrigation tube and said coring blade being aligned and having a configuration for passing a guidewire therethrough, the scythe shaped cutting edge of said primary homogenizing blade having a configuration for allowing the guidewire to pass through said coring blade, said coring blade, when translationally and rotationally driven, for serving to core the obstructive material, said homogenizing means, when rotationally driven, for homogenizing and mixing obstructive material within the hollow cylindrical passage of said coring blade with the fluid diluent in preparation for aspiration therefrom.

16. An atherectomy system for coring, homogenizing, and aspirating obstructive material from a body cavity or lumenal passage with the aid of a fluid diluent, the device comprising:

a catheter having a proximal end and distal end and defining an aspirating lumen extending therebetween, the distal end for passing through the body cavity, the proximal end for remaining outside the body cavity, a tubular bushing connector attached to the distal end of said catheter and extending therefrom, a coring blade defining a hollow cylindrical passage with a cutting edge for coring the obstructive material from the body cavity, said coring blade being set within the tubular bushing connector, extending distally therefrom, and freely rotatable therein, homogenizing means mounted for rotation and nested within the hollow cylindrical passage of said coring blade and bonded thereto for homogenizing the obstructive material therein, said homogenizing means defining a mixing chamber within said coring blade, a torque transmitting/irrigation tube housed within the aspirating lumen of said catheter for conducting fluid diluent into the mixing chamber of the homogenizing means for irrigating the homogenized occlusive material passing therethrough, said torque transmitting/irrigation tube being rotationally coupled to both said coring blade and said homogenizing means for rotationally driving same, a means for rotationally driving said torque transmitting/irrigation tube, said rotational driving means being attachable to said torque transmitting/irrigation tube at the proximal end of said catheter, a source of fluid diluent attachable to said torque transmitting/irrigation tube at the proximal end of said catheter for supplying fluid diluent thereto, said homogenizing means, when rotationally driven and when supplied with fluid diluent, for forming a homogenized mixture of obstructive material and fluid diluent within the hollow cylindrical passage of said coring blade suitable for aspiration out through the aspirating lumen of said catheter, and a means for drawing fluid, said fluid drawing means being connectable to the aspirating lumen of said catheter for aspirating the homogenized mixture of obstructive material and fluid diluent from the hollow cylindrical passage of said coring blade.

17. A method for coring and aspirating occlusive material from a body cavity or lumenal passage with the aid of a fluid diluent, the method comprising the following steps:

Step A: inserting a surgical catheter into the body cavity or lumenal passage and guiding the surgical catheter within the cavity or passage to the obstructive material; then Step B: simultaneously activating a coring blade located on the tip of the surgical catheter and a homogenizing means nested within a hollow cylindrical passage within the coring blade;

Step C: activating a source of fluid diluent for guiding the fluid diluent into the hollow cylindrical passage of the coring blade;

Step D: activating an aspirator for suctioning fluid from the hollow cylindrical passage of the coring blade; then Step E: coring the obstructive material within the cavity or passage by translating the coring blade into the obstructive material; while simultaneously Step F: homogenizing the cored obstructive material within the hollow cylindrical passage of the coring blade and forming a mixture of the homogenized obstructive material with the fluid diluent therein; and Step G: aspirating the mixture of homogenized obstructive material and fluid diluent from the hollow cylindrical passage of the coring blade; then Step H: simultaneously deactivating the homogenizing means, the fluid source, and the aspirator; and then Step I: withdrawing the surgical device from the cavity or passage.

* * * * *